(12) United States Patent
Lewandowski et al.

(10) Patent No.: US 8,765,113 B2
(45) Date of Patent: Jul. 1, 2014

(54) PEPTIDE BASED ANTIMICROBIAL COATING

(75) Inventors: Jan J. Lewandowski, South Euclid, OH (US); Yubaio Liu, Solon, OH (US)

(73) Assignee: Greatbatch Ltd., Clarence, NY (US)

( * ) Notice: Subject to any disclaimer, the term of this patent is extended or adjusted under 35 U.S.C. 154(b) by 15 days.

(21) Appl. No.: 13/534,164

(22) Filed: Jun. 27, 2012

(65) Prior Publication Data

US 2012/0328556 A1    Dec. 27, 2012

Related U.S. Application Data

(60) Provisional application No. 61/501,525, filed on Jun. 27, 2011.

(51) Int. Cl.
| | |
|---|---|
| *A01P 1/00* | (2006.01) |
| *A01N 37/46* | (2006.01) |
| *C08F 26/02* | (2006.01) |
| *C08F 8/30* | (2006.01) |
| *A61L 27/54* | (2006.01) |
| *A61L 29/16* | (2006.01) |
| *A61L 31/16* | (2006.01) |
| *A61L 33/12* | (2006.01) |
| *A61L 28/00* | (2006.01) |

(52) U.S. Cl.
CPC ............ *A61L 33/12* (2013.01); *A61L 2300/25* (2013.01); *A61L 28/0038* (2013.01); *A61L 31/16* (2013.01); *A61L 27/54* (2013.01); *A61L 2300/404* (2013.01); *A61L 29/16* (2013.01)
USPC .......... 424/78.27; 525/54.1; 424/407

(58) Field of Classification Search
CPC ............ A61L 2300/404; A61L 2300/25; A61L 29/16; A61L 33/12; A61L 28/0038; A61L 27/54; A61L 31/16
See application file for complete search history.

(56) References Cited

U.S. PATENT DOCUMENTS

| | | | |
|---|---|---|---|
| 7,282,214 | B2 | 10/2007 | Willcox et al. |
| 7,306,777 | B2 | 12/2007 | Bringley et al. |
| 7,976,863 | B2 | 7/2011 | Wilcox et al. |
| 2005/0079150 | A1 | 4/2005 | Gellman et al. |
| 2005/0107870 | A1 | 5/2005 | Wang et al. |
| 2006/0083772 | A1 | 4/2006 | DeWitt et al. |
| 2006/0115448 | A1 * | 6/2006 | Tew et al. .................... 424/78.3 |
| 2006/0239960 | A1 * | 10/2006 | Bossard et al. ............ 424/78.27 |
| 2009/0022888 | A1 | 1/2009 | Neff et al. |
| 2009/0155335 | A1 | 6/2009 | O'Shaughnessey et al. |

FOREIGN PATENT DOCUMENTS

| | | |
|---|---|---|
| WO | 2004022630 A2 | 3/2004 |
| WO | 2010057080 | 5/2010 |

OTHER PUBLICATIONS

Kenawy et al., Biomacromolecules, 8: 1361-1384 (2007).*
Palermo et al., Journal of Physical Chemistry B, 115: 566-375 (2011).*
Najjar et al., Letters in Applied Microbiology, 45: 13-18 (2007).*
Tai Y C et al: "Nisin antimicrobial activity and structural characteristics at hydrophobic surfaces coated with the PEO-PPO-PEO triblock surfactant Pluronic<(>R) F108", Journal of Colloid and Interface Science, vol. 322, No. 1, Jun. 1, 2008, pp. 104-111.
Vacheethasanee K., Marchant R.E.: "Surfactant polymers designed to suppress bacterial (Staphylococcus epidermidis) adhesion on biomaterials", J. Biomed. Mater. Res., vol. 50, No. 3, Jun. 5, 2000 pp. 302-312.
European Search Report dated Oct. 4, 2012.
Katanchalee Vacheethasanee et al., Poly(ethylene oxide) surfactant polymers, J. Biomater. Sci. Polymer Edn, vol. 15, No. 1, pp. 95-110(2004).
John W. M. Mulders et al., Identification and characterization of the lantibiotic nisin Z, a natural nisin variant, Eur. J. Biochem. 201, 581-584 (1991).
Onaizi et al., Tethering antimicrobial peptides: Current status and potential challenges, Sep. 3, 2010.
Janiak, Christopher et al., "The Vinyl Homopolymerization of Norborene" Macromol. Rapid Commun. 2001, 22, 479-492.

* cited by examiner

*Primary Examiner* — Daniel Sullivan
*Assistant Examiner* — Lisbeth C Robinson
(74) *Attorney, Agent, or Firm* — Steven W. Winn

(57) ABSTRACT

A comb-like surfactant polymer for changing the surface properties of biomaterials is described. The surfactant polymer comprises a polymeric backbone of repeating monomeric units having functional groups for chemically attaching to side chains, a plurality of hydrophobic side chains attached to the backbone via the functional groups and a plurality of hydrophilic side chains chemically attached via functional groups to the polymeric backbone. The hydrophilic side chains providing anti-thrombogenic properties to the surfactant. An antimicrobial agent selectively attached to some hydrophilic side chains thereby providing additional antimicrobial properties to the surfactant. The surfactant polymer may be applied to the surface of medical devices to reduce the surfaces thrombogenicity and decrease the number of microorganisms on the surface.

14 Claims, 7 Drawing Sheets

PEPTIDE BASED ANTIMICROBIAL COATING

CROSS REFERENCE TO RELATED APPLICATIONS

This application claims priority to U.S. provisional application Ser. No. 61/501,525, filed on Jun. 27, 2011.

BACKGROUND OF THE INVENTION

1. Field of the Invention

This invention relates generally to a surfactant polymer that comprises both non-thrombogenic and antimicrobial properties. More specifically, this invention relates to a surfactant polymer comprising a polymeric backbone of repeating monomeric units having functional groups for coupling with side chains, a plurality of hydrophobic side chains linked to the backbone via the functional groups, and a peptide based antimicrobial component linked to the backbone via the hydrophilic side chain. The antimicrobial surfactant may be applied to a surface of a medical device to impart the surfactant's non-thrombogenic and antimicrobial properties to the medical device surface.

2. Prior Art

The use of synthetic biomaterials to sustain, augment, or completely replace diseased human organs has increased tremendously over the past thirty years. Synthetic biomaterials are used in synthetic implants such as vascular grafts, heart valves, catheters and ventricular assist devices that have cardiovascular applications. Synthetic biomaterials are also used in extracorporeal systems and a wide range of invasive treatment, therapy delivery, and diagnostic systems. Unfortunately, existing biomaterials, suffer from well-known problems associated with surface-induced thrombosis or clot formation, such as thrombotic occlusion, thromboemboli, and infection.

Although the rate of infection is relatively low, the sheer volume of medical devices accounts for a large number of infections. For instance, for orthopedic implants, it has been reported that from the approximately 800,000 annually implanted devices in Europe, at least 1.5%, i.e., 12,000, peri-prosthetic infections will occur. Another device that has been associated with a high number of bloodstream infections is the central venous catheter. It is estimated that in the United States alone, at least 80,000 catheter related bloodstream infections (CRBSI) occur annually in intensive care units. Reports indicate that these CRBSIs are associated with as many as 24,000 patient deaths and increased health care costs ranging from approximately $10,000 to $30,000 per incidence. In many cases, the mean hospital stay is prolonged by at least 12 days, putting a heavy burden on the health care system as well as on patients and their families.

Besides infections, implanted medical devices may trigger a variety of other reactions, including inflammation, fibrosis and thrombosis. Undesired tissue responses can occur such as implant-associated protein adsorption and conformational changes which have been shown to promote blood coagulation and immune reactions. As a result, research efforts have been directed to reduce protein adsorption and cell interactions which subsequently improve biocompatibility.

One of the issues associated with catheters is thrombus formation on the surface of these devices. For example, central venous catheters (CVCs) are commonly used in blood and other bodily fluid exposed clinical practices. One of the foremost complications associated with their use is the potential for symptomatic or asymptomatic thrombosis. CVC thrombosis, in turn, may not only result in vascular and catheter occlusion but also infection, pulmonary embolism, and formation of right heart thromboemboli. Thrombi within cardiac chambers are associated with an increased risk of mortality due to their potential for embolization to the pulmonary vasculature. CVC thrombosis may also result in thrombo embolism of major organs. Estimates of CVC-related thrombosis vary depending on the site of insertion. For example, the incidence of thrombosis resulting from a peripherally inserted central catheter (PICC), in general, ranges from about 2% to about 4%. Pulmonary embolism is known to occur in approximately 15% of individuals with CVC related upper extremity deep vein thrombosis.

There have been several attempts to create nonthrombogenic surfaces on synthetic implants thereby increasing the blood-biocompatibility of implants. Early attempts included precoating the implants with proteins not involved in thrombosis, such as albumin, to mask the thrombogenic surface of the implant. However, such implants lose their non-thrombogenic properties within a short time. Attempts have been made to mask the thrombogenic surface by coating gelatin onto implants such as ventricular assist devices. While the gelatin coating reduced the thrombus formation, it did not adhere to the implant and it did not prevent thromboemboli and infection.

Attempts have also been made to render implants non-thrombogenic by coating the surface of the implant with polyethylene oxide to mask the thrombogenic surface of the implant. At times, this treatment has been known to reduce protein adsorption and thrombogenesis. However, the coupling of polyethylene glycol to the surface of the implant involves complex chemical immobilization procedures. Moreover, the coated implants do not consistently exhibit protein resistance because of the lack of control over the density of immobilized polyethylene oxide.

In addition, there have been many attempts to prepare non-thrombogenic surfaces by attaching anticoagulants such as heparin to biomaterials. However, each method requires complex immobilization procedures such that the implant surface is first modified by attachment of a coupling molecule before heparin can be attached. For example, the positively charged coupling agent tridodecylmethylammonium chloride (TDMAC) is coated onto an implant, which provides a positively charged surface and allows heparin, which has a high negative charge density, to be attached. However, the heparin slowly dissociates from the surface, to expose the positively charged TDMAC surface, which is particularly thrombogenic. Thus, the TDMAC heparin coated implant is successful only for short term implants such as catheters.

Furthermore, there have been many attempts to develop antimicrobial coatings. Among them are silver ion and antibiotic agent eluting mechanized coatings. These coating comprise either an antibiotic agent or have been impregnated with silver ions. These coatings are designed such that the antibiotic agent or the silver ions are released from the host coating material over a period of time.

Silver ion eluting coatings generally provide antimicrobial properties to a surface of a medical device. However, these coatings are known to increase thrombogeriicity of a surface and thus, could promote the formation of blood clots within the body. In addition, there has been concern about the potential negative side effects attributed to the elution of silver ions within the body.

Likewise, there is concern that microorganisms, such as bacteria, might become resistant to the antibiotic agent, thus reducing the effectiveness of such antibiotic eluting coatings. In addition, continued use of these antibiotic agents could, over time, promote the mutation of antibiotic resistant microorganisms, such as bacteria. Antibiotic eluting coatings are also constrained by the volume of the antibiotic agent therewithin. Therefore, once the antibiotic agent is exhausted from the host coating material, the antimicrobial properties of the coating are greatly diminished.

Antimicrobial peptides, on the other hand, naturally reside within many living organisms and are known to be generally biocompatible. Unlike anti-biotic and silver ion eluting coatings of the prior art, the present invention comprises a surfactant material within which the antimicrobial peptide resides within a localized area of the coating material and is not eluted further throughout the body.

The antimicrobial properties of these peptides result from the peptide's ability to disrupt the cell membrane of various bacteria. When an antimicrobial peptide comes into contact with a bacterial microorganism, the peptide renders the bacteria's cell membrane permeable, thus disrupting the cell structure such that the bacteria microorganism expires.

Despite these considerable research efforts, synthetic biomaterials, and medical devices made from such biomaterials, still suffer well-known problems associated with bacteria surface-induced thrombosis and bacterial infection. Accordingly, it is desirable to have new materials that can be used to coat biomaterials and to change their surface properties such that they are less likely to promote thrombogenicity and infection within the human body.

SUMMARY OF THE INVENTION

The present invention addresses both of the above issues, namely, protection of the patient from infection and thrombosis, resulting from the introduction of a medical device or implant within the body. The present invention provides a surfactant polymer comprising antithrombogenic properties that includes an antibacterial agent therewithin. The surfactant is designed to be applied onto a surface of a medical device, particularly an implantable medical device or implant, that is intended to be in contact with blood or other bodily fluids. More specifically, the surfactant of the present invention is designed to be applied to an exterior surface of a medical device or implant thereof, thus imparting the surfactant's antimicrobial and antithrombogenic properties to the coated surface.

When applied to a surface of a medical device or implant, the antimicrobial surfactant polymer of the present invention eliminates bacteria on contact, thus reducing the likelihood of contracting an infection from the introduction of the device or implant within the body. More specifically, the antimicrobial surfactant of the present invention inhibits the formation of a biofilm on the surface of the medical device or implant which could be a source of a systematic infection. At the same time, by improving the surfactant's antithromobogenic properties, implant fouling and implant related thromboembolism are reduced. Other advantages relate to the coating process, wherein the coating process for the present invention is compatible with different types of plastics used to fabricate various medical devices. Additionally, the surfactant does not require chemical activation of the surface that is being coated.

When a hydrophobic surface, such as polyurethane, polycarbonate, polystyrene and the like, is exposed to the surfactant polymer of the present invention, more specifically when the surfactant is in an aqueous solution, the surfactant attaches itself to the hydrophobic surface through hydrophobic moieties that are also attached to the backbone of the surfactant. Additionally, hydrophilic moieties such as polyethylene glycol, dextran, or combinations thereof may also be attached to the backbone of the surfactant polymer, thus providing antithrombogenic properties.

An antimicrobial agent, such as an antimicrobial peptide moiety, is attached to the ends of selected hydrophilic side chains, thereby imparting both antithrombogenic and antimicrobial properties to the surfactant. The antimicrobial peptide moieties are preferably attached via a tether and are oriented outwardly from the polymeric backbone. The tether, and outwardly extending orientation of the antimicrobial peptide from the backbone, increases the effectiveness of the surfactant's antimicrobial properties. The tether allows the antimicrobial peptide to intercept bacteria at a distance from the surface to which the peptide is applied.

In accordance with the present invention, novel, comblike, surfactant polymers useful for reducing the presence of microbials and thrombogenic effects on a surface, particularly, that of an external surface of an implanted medical device, is provided. Such surfactant polymers comprise a polymeric backbone of repeating monomeric units having functional groups for coupling with side chains, a plurality of hydrophobic side chains linked to the polymeric backbone via the functional groups, and a plurality of hydrophilic side chains linked to the backbone via the functional groups.

The hydrophobic side chains comprise an alkyl group $(CH_3(CH_2-)_n)$ comprising from about 2 to 18 methylene groups. The alkyl groups are linked to the polymeric backbone through ester linkages, secondary amine linkages, or, amide linkages. The hydrophilic side chain comprises molecules of polyethylene glycol, preferably dialdehyde-terminated polyethylene glycol, having an average molecular weight of less than 8,000 daltons, attached to the polymer backbone.

In addition, an antimicrobial agent, such as an antimicrobial peptide, is attached to an end of the hydrophilic chain. Nisin and the Nisin family of antimicrobial peptides are preferably attached to the distal end of the hydrophilic polyethylene glycol hydrophilic chain. In a preferred embodiment, the Nisin antimicrobial peptide is not attached to all hydrophilic chains. The antimicrobial peptide moieties are selectively attached to the ends of the hydrophilic chains such that both antithrombogenic properties stemming from the non attached hydrophilic chains coexist with the antimicrobial properties provided by the antimicrobial peptide. The antimicrobial peptide attaches to the distal end of the hydrophilic side chain via a functional group, preferably an aldehyde functional group.

DETAILED DESCRIPTION OF THE PREFERRED EMBODIMENT

The present invention provides novel comblike surfactant polymers that mimic the glycocalyx. The glycocalyx is the oligosaccharide-rich region on the surface of living cells. The glycocalyx serves to prevent undesirable biological adhesions, while proteins embedded in the cell membrane glycocalyx serve to promote desirable specific adhesions. In addition, an antimicrobial peptide is incorporated with the chemical structure of the glycocalyx mimicking surfactant polymer to provide additional antimicrobial properties to the surfactant.

Figure 1:
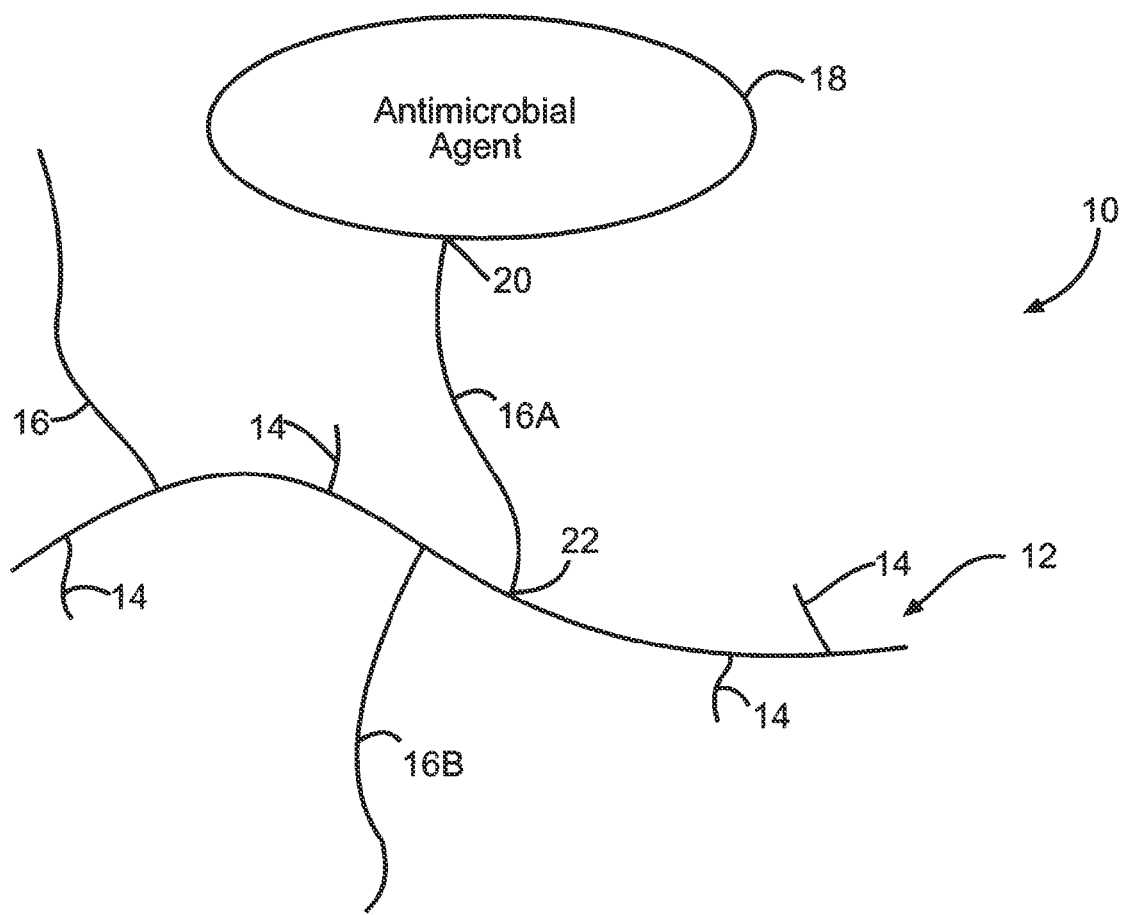
FIG. 1 illustrates a diagram of the antimicrobial surfactant of the present invention.
Figure 2:
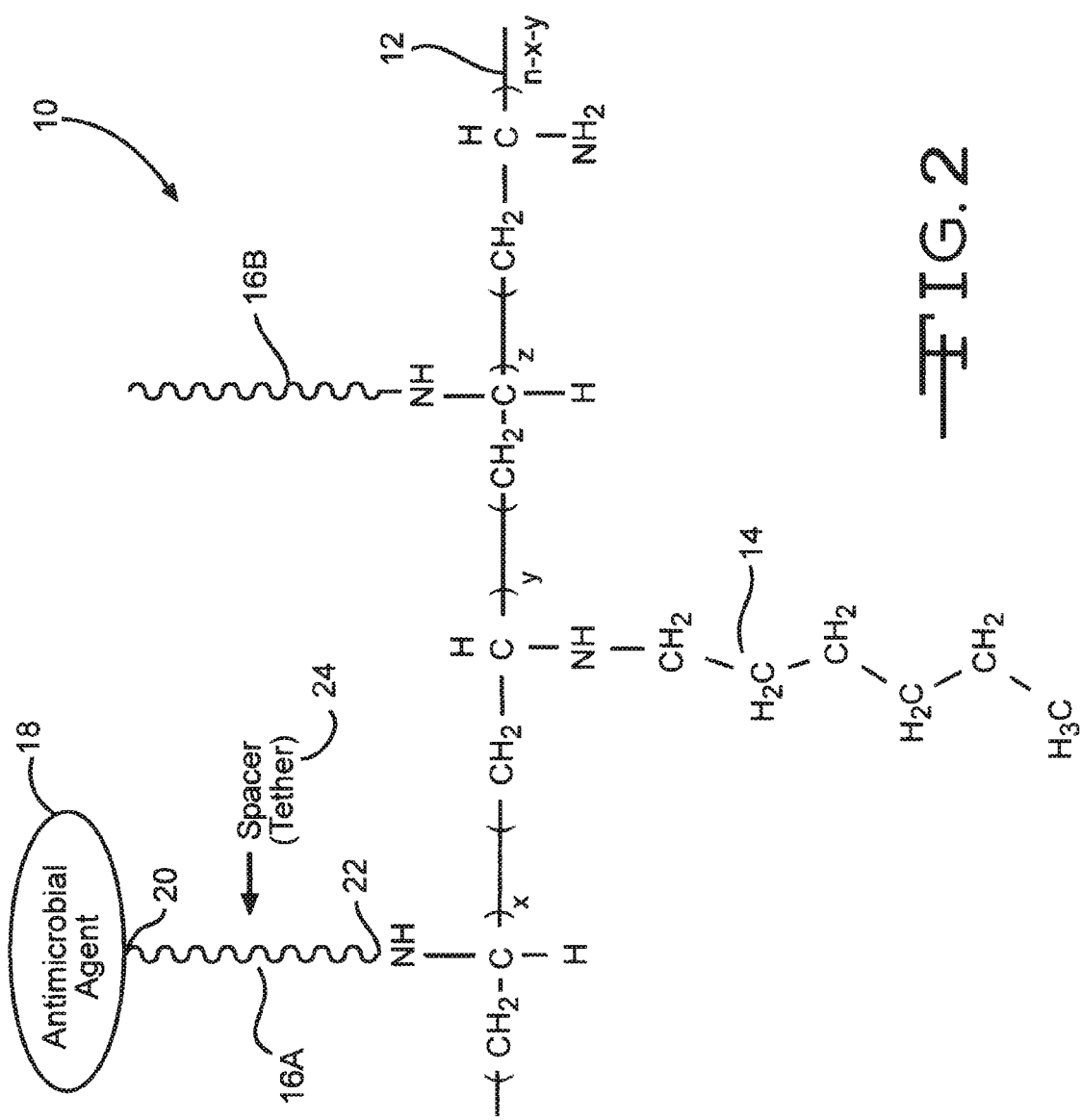
FIG. 2 shows an embodiment of the antimicrobial surfactant of the present invention.
Figure 3:
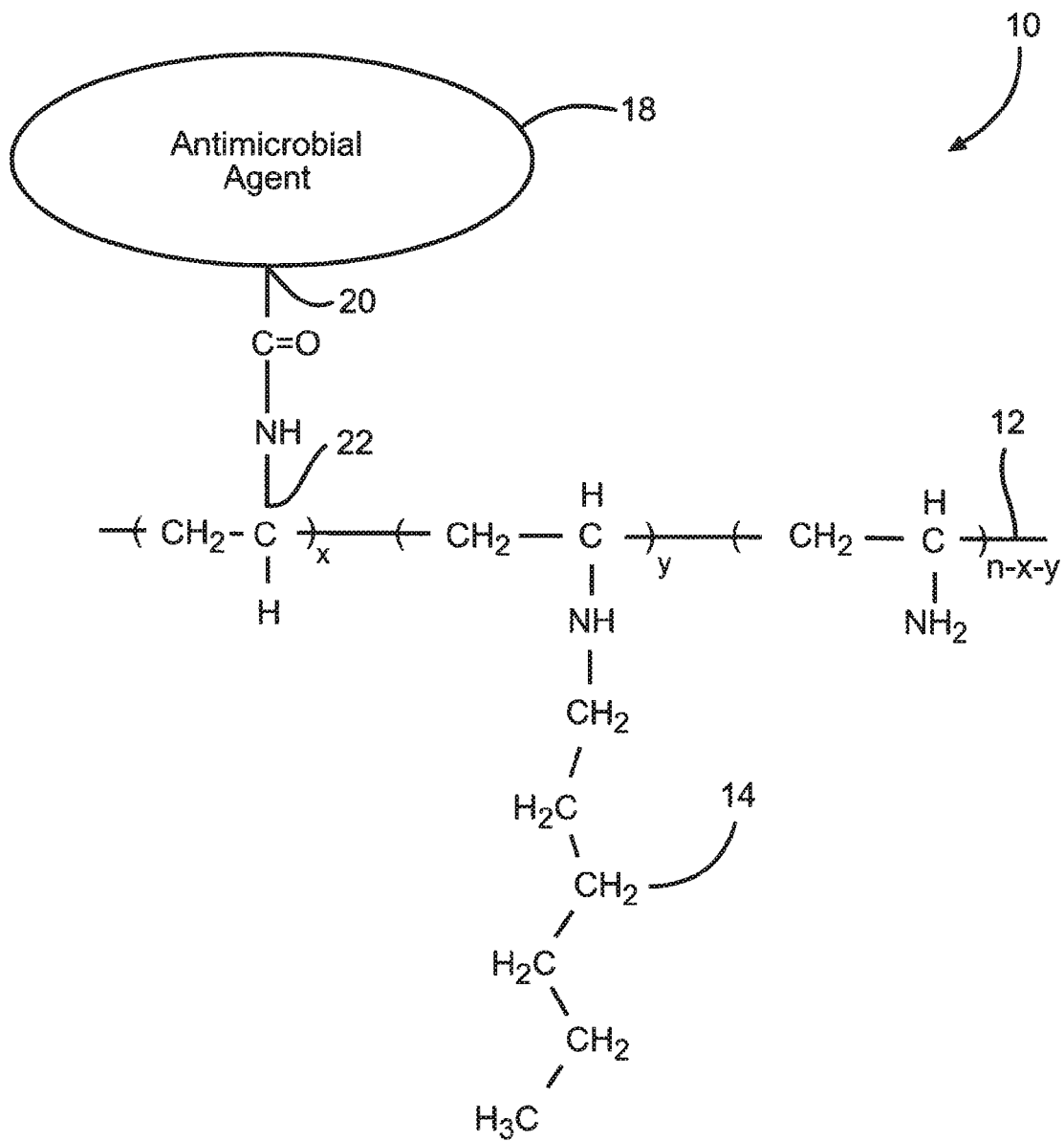
FIG. 3 illustrates an alternate embodiment of the chemical structure of the antimicrobial surfactant of the present invention.

Now referring to the figures, FIGS. 1-3 provide illustrations of embodiments of an antimicrobial surfactant polymer 10 of the present invention. FIG. 1 shows a generalized representation of the structure of the surfactant polymer of the present invention. As illustrated, the antimicrobial surfactant 10 comprises a polymeric backbone 12 preferably comprising polyvinyl amine (PVAm). A series of hydrophobic and hydrophilic molecular chains 14, 16 are attached to the backbone 12. The hydrophobic molecular chains 14 are provided as a means of attachment of the surfactant 10 to a hydrophobic surface such as a polymeric material through hydrophobic-to-hydrophobic interactions.

The hydrophilic molecular chains 16 are chemically attached to the backbone 12 and provide antithrombogenic properties to the surfactant 10. In general, these hydrophilic chains 16 block adhesion of nonspecific plasma proteins on the surface of the substrate. Furthermore, these hydrophilic chains 16 encourage anti-thrombogenity within the body. Thrombogenicity is a tendency of a material, such as the surface of an implanted medical device that is in contact with blood, to produce a thrombosis or blood clot. As such, these blood clots may become detached and travel through the blood stream. Blood clots, therefore, could become dislodged in the blood stream and impede the flow of blood to vital organs. Furthermore, these blood clots could become dislodged in the medical device, such as a catheter, blood pump, or introducer, thereby comprising the performance thereof. Examples of these hydrophilic chains 16 may comprise polyethylene glycol (PEG), dextran, and polysaccharide.

In a preferred embodiment of the present invention, an antimicrobial agent 18, such as an antimicrobial peptide, is selectively attached to an end of the hydrophilic chain 16. These antimicrobial agents 18, particularly antimicrobial peptides, are designed to eliminate bacteria on contact. Thus, the surfactant polymer 10 of the present invention comprises a plurality of hydrophilic chains 16, a certain percentage of which are chemically attached to the antimicrobial peptide agent 18. Therefore, the surfactant polymer 10 of the present invention comprises both anti-thrombogenic and anti-microbial properties.

The polymeric backbone 12 is conformationally flexible. Preferably, the polymeric backbone 12 is formed from a homopolymer that contains a plurality of functional side groups such as, for example, OH groups, COOH groups, or $NH_2$ groups. Although less preferred, the polymeric backbone may be formed from a copolymer which has a combination of functional side groups. For example, the copolymer may have OH side groups and $NH_2$ side groups. Suitable homopolymers for forming the comblike surfactant polymer are, by way of example, polylysine, poly(vinyl alcohol) or poly(vinyl amine). Preferably, the polymeric backbone 12 is formed from a poly(vinyl amine) (PVAm).

In a preferred embodiment of the present invention, an antimicrobial agent 18, such as an antimicrobial peptide, is selectively attached to an end of the hydrophilic chain 16. These antimicrobial agents 18, particularly antimicrobial peptides, are designed to eliminate bacteria on contact. Thus, the surfactant polymer 10 of the present invention comprises a plurality of hydrophilic chains 16, a certain percentage of which are chemically attached to the antimicrobial peptide agent 18. Therefore, the surfactant polymer 10 of the present invention comprises both anti-thrombogenic and anti-microbial properties.

The hydrophilic side chain 16 is selected from hydrophilic moieties comprising amine, amide, or, more preferably, aldehyde functional groups. In an embodiment, the hydrophilic side chain 16 comprises polyethylene glycol, and most preferably, dialdehyde-terminated polyethylene glycol (PEG-diCHO). The PEG-diCHO hydrophilic side chain 16 is prepared by oxidation of the terminal hydroxyl group of the polyethylene glycol. The hydrophilic side chains 16 are linked to the polymeric backbone 12 through an ester linkage, an aldehyde linkage, an amide linkage or preferably a secondary amine linkage. In a preferred embodiment a plurality of PEG or PEG-diCHO hydrophilic chains 16 are attached to the polymeric backbone 12 via a secondary amine linkage.

The hydrophilic side chains 16 may also be formed from oligosaccharides such as, for example, the oligosaccharides that are obtained from heparin. The heparin oligosaccharides are hydrated and negatively charged which provides an additional electrostatic repulsive force that further repels plasma proteins and cellular elements such as platelets. The heparin oligosaccharide contains the unique pentasaccharide sequence that is essential for heparin's anticoagulant activity. The heparin product of deaminative cleavage of heparin may possess a terminal 2,5 anhydromanose unit. In a preferred embodiment, the terminal aldehyde of the 2,5 anhydromannose is reacted with the amines on the polymeric backbone to form a chemical bond. Other suitable charged oligosaccharides for forming coatings which are non-adhesive for plasma proteins include dermatan sulfate, and dextran sulfate, which are hydrated and negatively charged and serve to repulse proteins and platelets.

As shown in FIGS. 1-3 an antimicrobial agent 18 is attached to a distal end 20 of the hydrophilic chain 16. More specifically, an antimicrobial peptide is selectively attached to the functional group, located at the distal end 20 of the hydrophilic moiety 16. At the opposite end of the chain, the polymeric backbone 12 is attached at a proximal end 22 of the hydrophilic side chain 16. Antimicrobial peptides have been demonstrated to kill Gram negative and Gram positive bacteria (including strains that are resistant to conventional antibiotics), mycobacteria (including mycobacterium tuberculosis), enveloped viruses, fungi and even transformed or cancerous cells. Antimicrobial peptides generally comprise between 12 and 50 amino acids. These peptides generally include two or more positively charged residues provided by arginine, lysine or, in acidic environments, histidine, and a large proportion (generally >50%) of hydrophobic residues.

Figure 4:
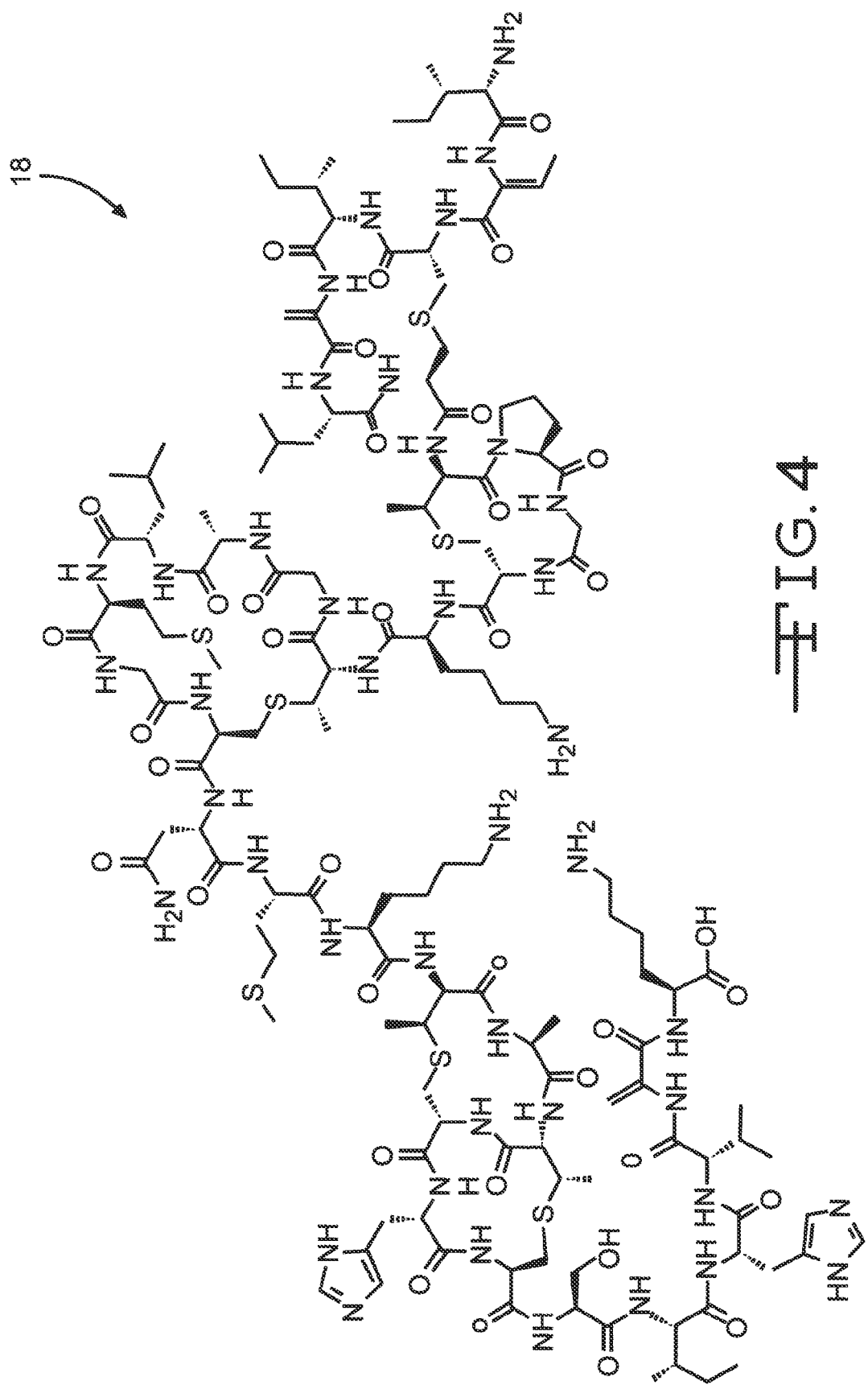
FIG. 4 shows a chemical model of an embodiment of an antimicrobial agent according to the present invention.

A preferred antimicrobial peptide 18 comprises Nisin and the Nisin family of antimicrobial peptides. Nisin is an example of a "broad-spectrum" bacteriocin that is effective in eliminating many Gram-positive organisms, including lactic acid bacteria (commonly associated with spoilage), *listeria monocytogenes* (a known pathogen), *staphylococcus aureus*, bacillus cereus, and Clostridium botulinum. Nisin is a polycyclic antibacterial peptide comprising 34 amino acid residues that are commonly used as a food preservative. Nisin contains the uncommon amino acids lanthionine (Lan), methyllanthionine (MeLan), didehydroalanine (Dha) and didehydroaminobutyric acid (Dhb). A representative embodiment of the chemical structure of a Nisin molecule is shown in FIG. 4. The Nisin family of antimicrobial peptides comprises Nisin A, Nisin Q, Nisin F, Nisin Z, Nisin Q, Nisin F, and Nisin U. Although Nisin is a preferred antimicrobial agent 18, other antimicrobial peptides may also be used. For example, the antimicrobial agent 18 may be selected from a multitude of antimicrobial peptides that are linkable to a polyethylene glycol molecular chain comprising an aldehyde terminal functional group.

As shown in FIGS. 1-3, the antimicrobial agent 18 is chemically attached to the distal end 20 of the hydrophilic chain 16 via the hydrophilic chain's functional group. In a preferred embodiment, the antimicrobial peptide, particularly Nisin, is attached to an aldehyde functional group.

In a preferred embodiment, the antimicrobial surfactant polymer 10 of the present invention comprises a first polyethylene glycol polymer hydrophilic chain 16A, in which an aldehyde functional group resides at both the distal and proximal ends 20, 22 of the hydrophilic chain 16. The proximal hydrophilic end 22, is attached to the PVAm backbone 12, via a first aldehyde functional group, and the hydrophilic chain distal end 20, is attached to Nisin via a second aldehyde functional group. A second polyethylene glycol polymer hydrophilic chain 16B, comprising various function groups, particularly an aldehyde functional group, at both distal and proximal ends 20, 22 may be attached to the backbone 12 of the polymer 10. However, the distal end 20 of this second polyethylene glycol polymer hydrophilic chain 16B may or may not be attached to the antimicrobial agent 18, such as a Nisin antimicrobial peptide moiety.

As illustrated in FIG. 2, the antimicrobial agent 18, such as Nisin, may be attached to a tether 24 that is attached to the backbone 12 of the surfactant polymer 10. The tether 24 may comprise an elongated hydrophilic chain 16 that preferably comprises an aldehyde functional group at both proximal and distal ends. The tether 24 enables the antimicrobial agent 18 to be spaced away from the surface of the medical device or implant (not shown).

This embodiment is preferred in that it enables the antimicrobial agent 18 to eliminate bacteria and other undesirable organisms before they come near to the surface of the substrate, such as the exterior surface of a medical device, particularly an implantable medical device, or implant. In addition, the tether 24 allows the antimicrobial agent 18, particularly Nisin, to freely move within the surrounding blood and bodily fluids. Thus, the antimicrobial agent 18 is enabled to float freely within the blood stream near the substrate surface and eliminate bacteria therewithin. In other words, the tether 24 allows the antimicrobial peptide 18 to intercept bacteria sooner before coming into contact with the surface of the device or implant.

The term "medical device" is defined herein as an instrument, apparatus, implement, machine, contrivance, implant, in vitro reagent, or other similar or related article, including a component part, or accessory which is: recognized in the official National Formulary, or the United States Pharmacopoeia, or any supplement to them, intended for use in the diagnosis of disease or other conditions, or in the cure, mitigation, treatment, or prevention of disease, in man or other animals, or intended to affect the structure or any function of the body of man or other animals, and which does not achieve any of it's primary intended purposes through chemical action within or on the body of man or other animals and which is not dependent upon being metabolized for the achievement of any of its primary intended purposes.

The ratio of hydrophobic side chains 14 to hydrophilic polyethylene glycol chains 16 on the polymer backbone 12 is designed to achieve a hydrophilic to hydrophobic balance that allows the surfactant. 10 to adsorb onto the hydrophobic surface of the biomaterial. The hydrophilic to hydrophobic balance depends on the density of the hydrophobic and hydrophilic side chains 14, 16 and the length of the hydrophobic side chains 14 and hydrophilic side chains 16. Adhesion of the adsorbing polymer onto the hydrophobic surface of the biomaterial is enhanced by increasing the length, i.e., the number of methylene groups of the hydrophobic side chain 14, by increasing the density of the hydrophobic side chains relative to the hydrophilic side chains, and/or by reducing the length of the hydrophilic side chains.

The ratio of antimicrobial agent 18 terminated to non-antimicrobial agent terminated hydrophilic molecular side chains 16 can also be adjusted. By adjusting the ratio of hydrophilic side chains comprising the antimicrobial agent to those that do not, the balance of anti-thrombogenic and antimicrobial properties can be modified. For example, increasing the amount of antimicrobial agent 18 within a given number of hydrophilic side chains 16 within the surfactant 10 increases the surfactant's antimicrobial properties. Likewise, reducing the number of antimicrobial agents 18 within a given amount of hydrophilic chains 16 generally increases the surfactant's antithombogenic properties.

Figure 5:
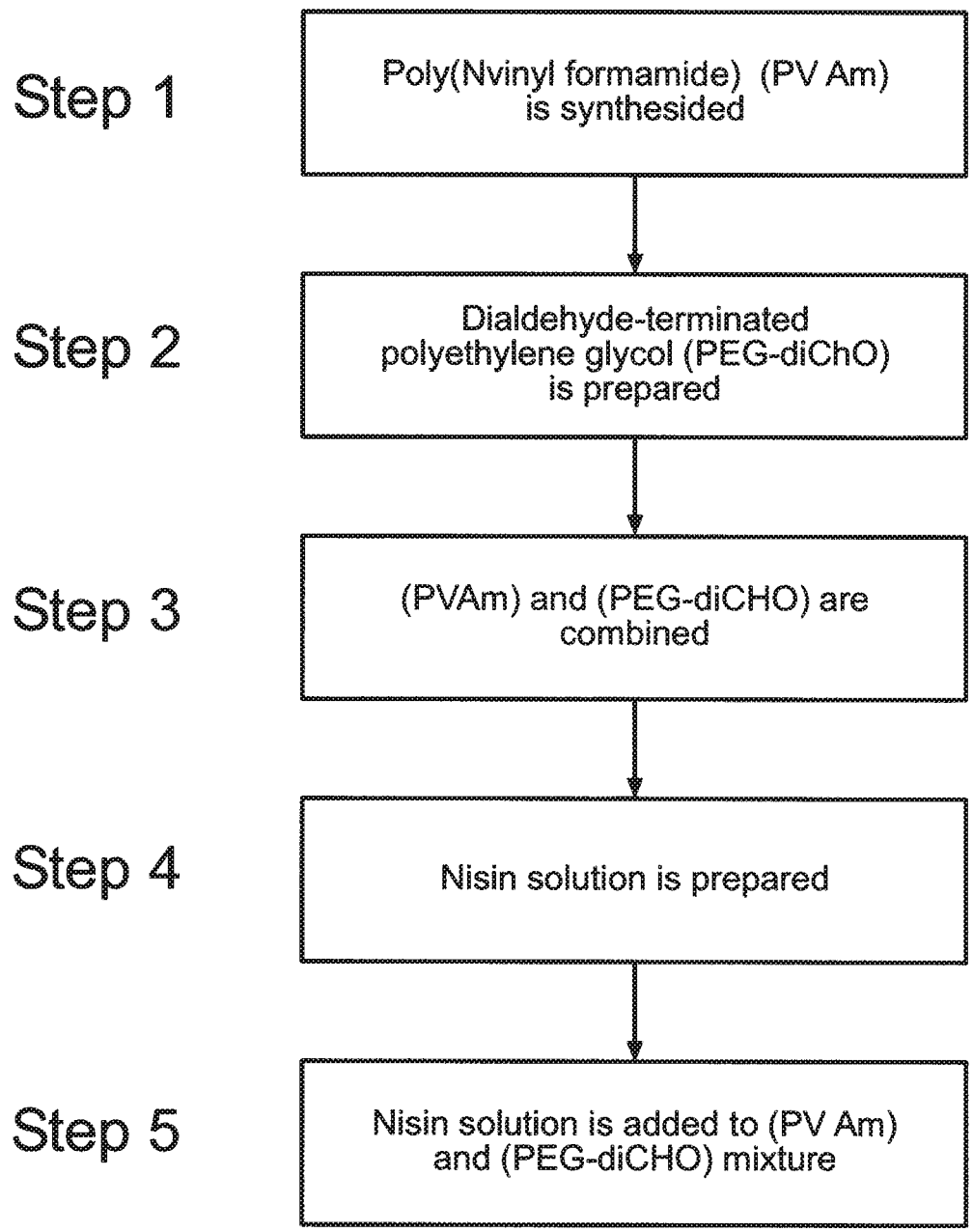
FIG. 5 illustrates a flow chart of the fabrication of the antimicrobial surfactant of the present invention.

Synthesis of the surfactant polymer 10 of the present invention generally comprises the steps of first synthesizing the polyvinylamine (PVAm) polymer from poly(N-vinyl formamide). As shown in the flow chart of FIG. 5, the poly(N-vinyl formamide) is prepared through a free radical polymerization process using azobisisobutyronitrile (AIBN) as an initiator and isopropanol as the solvent. The poly(N-vinyl formamide) is then hydrolyzed in a basic condition. Hydrochloric acid (HCl) is then added to form a polyvinyl amine hydrochloride salt. This salt is then converted to polyvinyl amine through ion exchange using a strong anionic resin. The final PVAm polymer was obtained through extensive dialysis against water, preferably deionized water, followed by lyophilization.

Second, the hydrophilic chain 14 is formulated. In an embodiment, dialdehyde-terminated polyethylene glycol (PEG-diCHO) is prepared by oxidation of the terminal hydroxyl group of the polyethylene glycol. In a preferred embodiment, 2,000 molecular weight polyethylene glycol (PEG) is dissolved in dimethyl sulfoxide (DMSO). Acetic anhydride, preferably of a 40:1 mol ratio of anhydride to hydroxyl, is added to the PEG at room temperature. When fully reacted, the mixture is precipitated in diethyl ether. The precipitate is dissolved in methylene chloride and then re-precipitated in diethyl ether. The product is then filtered and vacuum dried overnight at room temperature to yield PEG-diCHO.

Third, the final antimicrobial surfactant (PVAm/PEG:Hex:Nisin) of the present invention is formulated. The previously prepared dialdehyde-terminated polyethylene glycol and polyvinylamine is combined with hexanal in the presence of sodium cyanoborohydride using reductive amination. Nisin is then attached to the polyethylene glycol segment to the unreacted aldehyde end groups utilizing reductive amination.

EXAMPLES

For the following surfactant examples, acetic ahydride, dimethyl sulfoxide and chloroform were obtained from Sigma Aldrich and were used as received. Hexanal and polyethylene glycol 2000 were obtained from Alfa Aesar and used as received. Sodium cyanoborohydride, received from ACROS organics, was used as received. Diethyl ether, sodium hydroxide and hydrochloric acid were obtained from Fisher Scientific and were used as received. Nisin ZP®, received from Handary S. A. Belgium, was used as received.

The surfactant polymers were synthesized by first linking dialdehyde-terminated polyethylene oxide (PEG-diCHO) and hexanal to polyvinyl amine simultaneously in the presence of sodium cyanoborohydride, using the method of reductive amination. The PEG-diCHO was prepared by oxidizing the terminal hydroxyl groups of polyethylene glycol molecules using a modified process published in the *J. Poiym. Sci. Polym. Chem.* 1984, vol. 22, p. 341 by Harris et al.

In the process, about 10 g. of polyethylene glycol 2000 (5 mmol) was dissolved in about 17 ml of DSMO. Next, about 20 g. of acetic anhydride (40:1 mol ratio of anhydride to hydroxyl) was added to the mixture and stirred for about 8 hours at room temperature. At the end of the reaction, the solution was precipitated in about 700 ml of diethyl ether. The precipitate was re-dissolved in methylene chloride and re-precipitated in about 200 ml of diethyl ether, three consecutive times. The product was vacuum dried for about 8 to 12 hours to yield PEG-diCHO having an $^1$H-NMR (ppm) of 3.2 to 3.6 ($CH_9CH_2O$).

After the PVAm/PEG:Hex was prepared, Nisin was then attached to the unreacted aldehyde end groups of the polyethylene glycol segment by reductive amination. Reductive amination is a process by which an amine group is introduced into an organic molecule. More specifically, reductive amination is a process in which an imine double bond is reduced to a carbon-nitrogen single bond. It is noted that the amounts of the chemical components described in the examples herein may be proportionally increased to increase the volume and yield of the final surfactant polymer produced.

Example 1

Antimicrobial surfactant polymer (PVAm/PEG:Hex:Nisin) with a mole feed ratio of PEG-diCHO to hexanal of 1:2 and a mole feed ratio of Nisin to PEG-diCHO of 1:10 was prepared.

In this example, 1.55 grams of PEG-diCHO (0.775 mmol) was dissolved in 15 mL of methanol at room temperature. In a separate container, 100 mg of PVAm (2.32 mmol amine group) was dissolved in 15 mL of methanol. 0.1552 g of hexanal (1.55 mmol) was then added to the PVAm mixture at room temperature with constant stirring for about an hour. The resulting solution was then mixed with the PEG-diCHO solution, the resulting mixture was left to react for 24 hours at room temperature. Next, 0.26 g of Nisin (0.077 mmol) was mixed with 200 mL of methanol under magnetic stirring. 4 M HCl was slowly added to the Nisin methanol mixture to aid in the dissolution of the Nisin in the methanol. 5 M NaOH was subsequently added to neutralize the Nisin solution to a pH of about 5~6. The neutralized Nisin solution was then added in a drop wise manner to the PVAm-PEG-Hex solution. 0.1656 g of sodium cyanoborohydride (2.64 mmol), dissolved in 1 mL of methanol, was added to the mixture. The mixture was allowed to react for 24 hours. The polymer product was purified by dialysis using a Spectra/Por® dialysis membrane (MWCO 25K) for 2 days against fresh Milli-Q water. The final polymer product was obtained by lyophilization.

Example 2

Antimicrobial surfactant polymer (PVAm/PEG:Hex:Nisin) with a mole feed ratio of PEG-diCHO to hexanal of 1:1 and a mole feed ratio of Nisin to PEG-diCHO of 1:10 was prepared.

In this example, 2.325 g of PEG-diCHO (1.16 mmol) was dissolved in 15 mL of methanol at room temperature. In a separate container, 100 mg of PVAm (2.32 mmol amine group) was added to 15 mL of methanol, 0.1161 g of hexanal (1.16 mmol) was added at room temperature with constant stirring for an hour. The two mixtures were combined and left to react for 24 hours at room temperature. Next, 0.39 g of Nisin (0.116 mmol) was mixed with 200 mL of methanol under magnetic stirring. 4 N HCl was added to the solution to aid the dissolution of Nisin in the methanol. 5 M NaOH was added to the Nisin solution to neutralize the Nisin solution to a pH of 56, The Nisin solution was then added to the PVAm-PEG-Hex mixture in a drop wise manner. 0.1753 g of sodium cyanoborohydride (2.79 mmol), mixed with 1 mL of methanol, was added into the above mixture to adjust the reaction of the mixture to a pH of 5~6. The reaction was allowed to proceed for 24 hours at room temperature. The polymer product was purified by dialysis using Spectra/Por® dialysis membrane (MWCO 25K) for 2 days against fresh Milli-Q water. The final polymer product was obtained by lyophilization.

Example 3

Antimicrobial surfactant polymer (PVAm/PEG:Hex:Nisin) with a mole feed ratio of PEG-diCHO to hexanal of 1:1 and a mole feed ratio of Nisin to PEG-diCHO of 1:2 was prepared.

In this example, 2.325 g of PEG-diCHO (1.16 mmol) was dissolved in 15 mL of methanol at room temperature. In a separate container, 100 mg of PVAm (2.32 mmol amine group) was dissolved in 15 mL of methanol. Next, 0.1164 g of hexanal (1.16 mmol) was added to the PVAm mixture at room temperature with constant stirring for an hour. The PVAm hexanal mixture was then combined with the PEG-diCHO solution, allowing the reaction to proceed for 24 hours at room temperature. Next, 1.9491 g of Nisin (0.58 mmol), was mixed with 200 mL of methanol under magnetic stirring. 4 M HCl was then added to aid in the dissolution of the Nisin in the methanol. 5 M NaOH was then added to neutralize the Nisin solution back to a pH of 5~6. The Nisin solution was then added to the PVAm-PEG-Hex mixture in a drop wise manner. Next, 0.2178 g of sodium cyanoborohydride (3.48 mmol), dissolved in 1 mL of methanol, was added to the mixture to adjust the mixture to a pH of 5~6. The mixture was left to react for 24 hours. The polymer product was purified by dialysis using Spectra/Por® dialysis membrane (MWCO 25K) for 2 days against fresh Milli-Q water. The final polymer product was obtained by lyophilization.

Example 4

Antimicrobial surfactant polymer (PVAm/PEG:Hex:Nisin) with a mole feed ratio of PEG-diCHO to hexanal of 1:2 and a mole feed ratio of Nisin to PEG-diCHO of 3:4 was prepared.

In this example, 1.55 g of PEG-diCHO (0.775 mmol) was dissolved in 15 mL of methanol at room temperature. In a separate container 100 mg of PVAm (2.32 mmol amine group) was added to 15 mL of methanol, to which 0.1552 g of hexanal (1.55 mmol) was added at room temperature with constant stirring for about an hour. The solution was combined with the PEG-diCHO solution allowing the reaction, to proceed for 24 hours at room temperature. In a separate container, 1.9491 g of Nisin (0.58 mmol) was mixed with 200 mL of methanol under magnetic stirring, 4 M HCl was added to aid the dissolution of Nisin in the methanol. 5 M NaOH was added to neutralize the Nisin solution back to a pH 5~6. The Nisin solution was added in a dropwise manner to the PVAm-PEG-Hex mixture. Next, 0.1948 g of sodium cyanoborohydride (3.1 mmol), mixed in 1 mL methanol, was added to the mixture to further adjust the reaction mixture pH to 5~6. The reaction was allowed to proceed for 24 hours. The polymer product was purified by dialysis using Spectra/Por® dialysis membrane (MWCO 25K) for 2 days against fresh Milli-Q water. The final polymer product was obtained by lyophilization.

Example 5

Antimicrobial surfactant polymer (PVAm/PEG:Hex:Nisin) with a mole feed ratio of PEG-diCHO to hexanal of 2:3 and a mole feed ratio of Nisin to PEG-diCHO of 1:4 was prepared.

In this example, 1.86 g of PEG-diCHO (0.93 mmol) was added to 15 mL of methanol at room temperature. In a separate container, 100 mg of PVAm (2.32 mmol amine group) was mixed with 15 mL of methanol. 0.1397 g of hexanal (1.39 mmol) was then added to the PVAm mixture at room temperature under constant stirring for about an hour. The PVAm-hexanal mixture was then combined with PEG-diCHO solution and allowed to react for 24 hours at room temperature. In another separate container, 0.7796 g of Nisin (0.23 mmol) was mixed with 200 mL of Milli-Q water under magnetic stirring. 4 M HCl was added to aid the dissolution of Nisin in the water. 5 M NaOH was then added to the Nisin solution to neutralize the solution back to a pH of 5~6. The neutralized Nisin was then added to the PVAm-PEG-Hex mixture in a drop wise manner. Then 0.2045 g of sodium cyanoborohydride (3.26 mmol), mixed in 1 mL of methanol, was added to the above mixture. The reaction was allowed to proceed for 24 hours. The polymer product was purified by dialysis using Spectra/Por® dialysis membrane (MWCO 25K) for 2 days against fresh Milli-Q water, The final polymer product was obtained by lyophilization.

Example 6

Antimicrobial surfactant polymer (PVAm/PEG:Hex:Nisin) with a mole feed ratio of PEG-diCHO to hexanal of 1:2 and a mole feed ratio of Nisin to PEG-diCHO of 3:10 was prepared.

In this example, 1.55 g of PEG-diCHO (0.775 mmol) was added to 15 mL, of methanol at room temperature. In a separate container, 100 mg of PVAm (2.32 mmol amine groups) was added to 15 mL of methanol. 0.1552 g of hexanal (1.55 mmol) was added to the PVAm mixture at room temperature under constant stirring for about an hour. The PVAm-hexanal mixture was then combined with PEG-diCHO solution, allowing the reaction to proceed for 24 hours at room temperature. In a separate container, 0.7796 g of Nisin (0.23 mmol) was mixed with 200 mL Milli-Q water under magnetic stirring. 4 M HCl was added to aid in the dissolution of Nisin in the water. 5 M NaOH was then added to neutralize the Nisin solution back to a pH 5~6. The neutralized Nisin solution was then added to the PVAm-PEG-Hex mixture in a drop wise manner. 0.195 g of sodium cyanoborohydride (3.1 mmol), mixed in 1 mL of methanol was then added to the above mixture to adjust the reaction mixture to a pH of 5~6. The reaction was then allowed to proceed for 24 hours, The polymer product was purified by dialysis using Spectra/Por® dialysis membrane (MWCO 25K) for 2 days against fresh Milli-Q water. The final polymer product was obtained by lyophilization.

Figure 6:
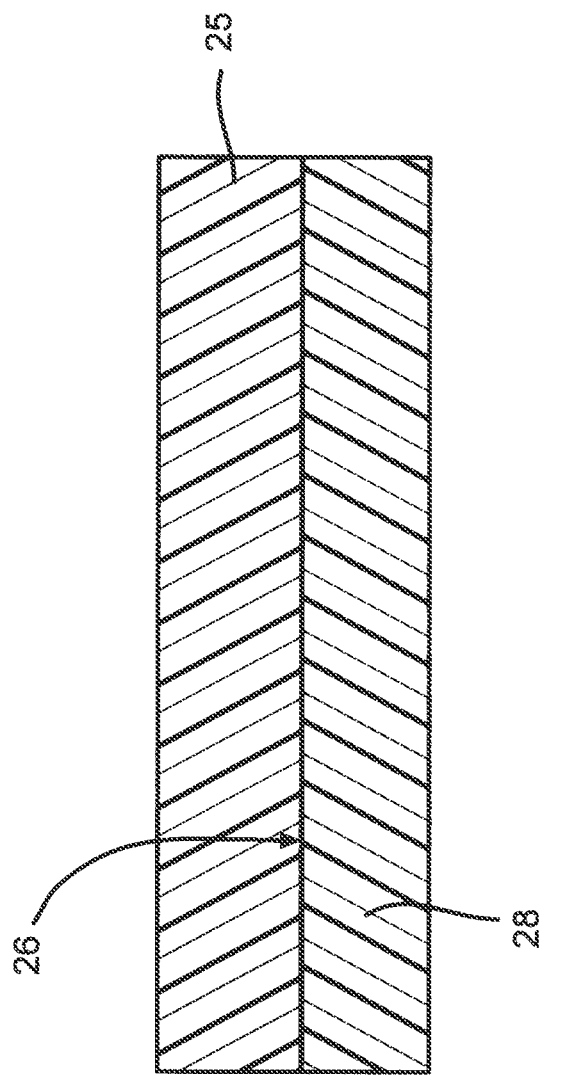
FIG. 6 shows an embodiment of the antimicrobial surfactant applied to a surface of a substrate.

Once the antimicrobial surfactant 10 has been formulated, as shown and described, it is then preferably applied to a surface 26 of a substrate 28. As shown in FIG. 6, the surfactant 10 is applied as a coating layer 25 to the surface 26 of the substrate. In a preferred embodiment, the surface 26 of the substrate 28 may comprise the surface of a medical device, particularly the exterior surface of the medical device that is in contact with blood and/or other bodily fluids.

The medical device is non-limiting and may comprise a catheter, an introducer, a medical lead, a cardiac defibrillator, a cardiac pacemaker, a neuro-stimulator, a drug pump, a blood pump, a heart valve, an orthopedic implant, an orthopedic tool, and the like.

In a preferred embodiment, the antimicrobial surfactant of the present invention 10 is applied to a surface 26 that is hydrophobic. A hydrophobic surface encourages a hydrophobic-to-hydrophobic interaction with the hydrophobic polymer chains 14 of the surfactant 10.

Figure 7:
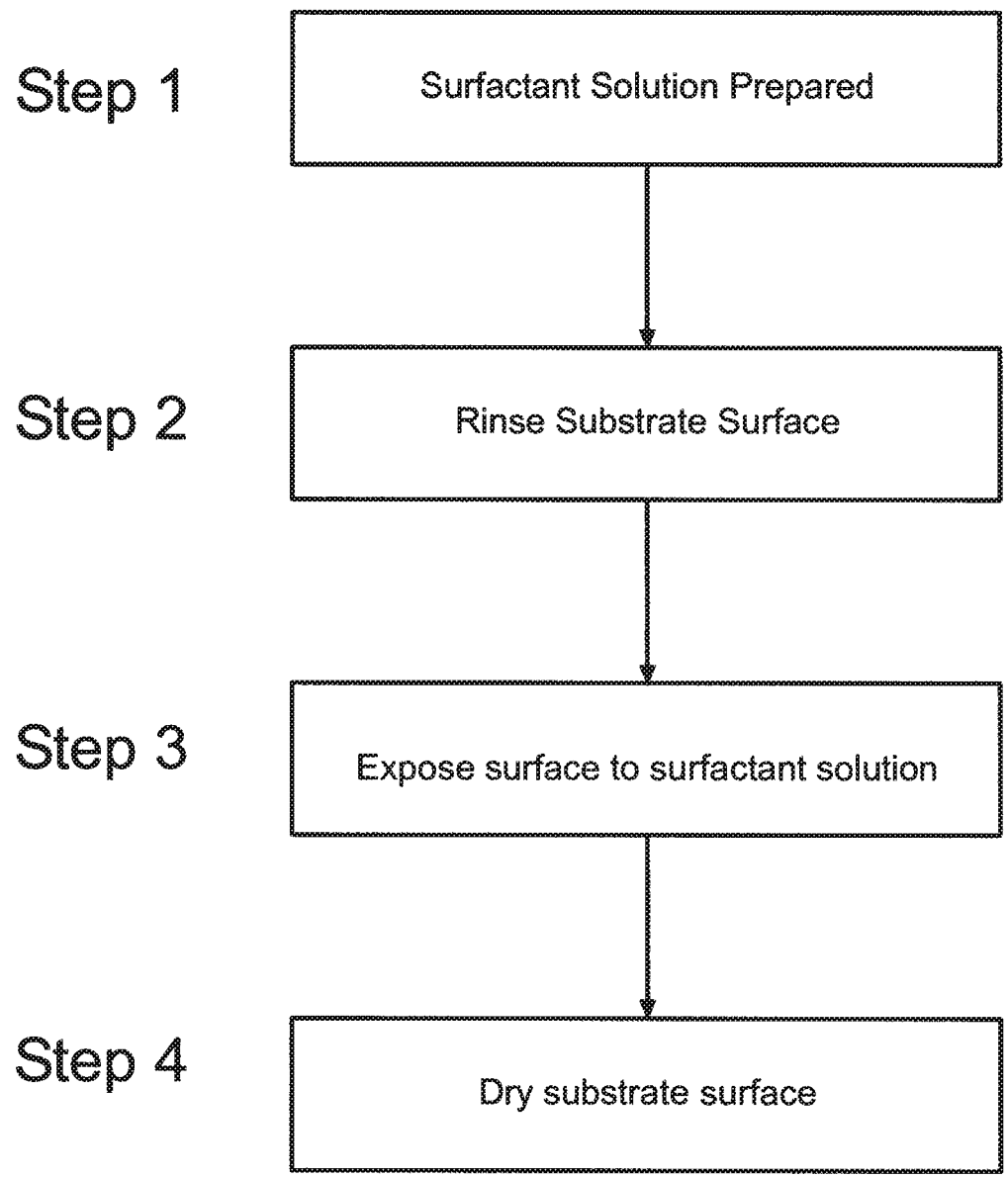
FIG. 7 illustrates a flow chart of an embodiment of the application process of the surfactant.

In a preferred embodiment, the antimicrobial surfactant 10 is applied to the surface 26 of the substrate 28 by exposing the surface to a solution comprising the surfactant 10 and water. FIG. 7 illustrates a flow chart of the surfactant application process. In an embodiment of the antimicrobial surfactant application process, a surfactant solution is first prepared by dissolving the surfactant polymer in water, preferably deionized water, to a concentration ranging from about 0.1 percent to about 1.0 percent, preferably about 0.2 percent, by volume. Second, the surface 26 to which the surfactant is to be coated, is prepared by rinsing the surface 26 in a mixture of about 10 percent isopropyl alcohol deionized water solution. Agitation may be used to remove undesired surface contaminants if desired. After the surface is rinsed, the surface is dried and exposed to the surfactant water solution.

In a preferred embodiment, the surface 26 is exposed to the surfactant water solution for about 10 to about 20 hours at a temperature ranging from about 35° C. to about 45° C. The surfactant solution may be applied to the surface 26 in a multitude of ways. For example, the surface 26 may be dipped coated, spray coated, spin coated, or applied with a brush. After the coating 25 has adhered to the surface 26, it is dried and rinsed thoroughly in deionized water.

Thus, the present invention teaches various formulations and methods of incorporation of a biomimetic surfactant comprising an antimicrobial peptide onto the substrate of a medical device. The thusly modified substrate has improved infacial blood compatibility including the ability to prevent blood clots and minimize bacterial infection. This makes the polymeric material a desirable candidate for use in the manufacture of implantable medical devices.

What is claimed is:

1. An antimicrobial surfactant polymer, comprising:
   a) a polymeric backbone of repeating monomeric units;
   b) a plurality of hydrophobic side chains comprising from about 2 to about 18 methylene groups, the plurality of hydrophobic side chains being linked to the polymeric backbone by one of the group consisting of ester linkages, secondary amine linkages, amide linkages, and combinations thereof;
   c) an antimicrobial peptide comprising Nisin having an aldehyde linkage;
   d) a first hydrophilic side chain and a second hydrophilic side chain having spaced apart proximal and distal chain ends comprising reactionable di-aldehyde terminated polyethylene glycol molecules, wherein the proximal end of the first and second hydrophilic side chains are linked to the polymeric backbone by one of the group consisting of an ester linkage, a secondary amine linkage, an amide linkage, and combinations thereof; and
   e) wherein the distal end of at least one of the first or second hydrophilic side chains is linked to the antimicrobial peptide by an aldehyde linkage.

2. The antimicrobial surfactant polymer of claim 1 wherein the antimicrobial peptide is selected from the group consisting of Nisin A, Nisin Z, Nisin Q, Nisin F, Nisin U, and combinations thereof.

3. The antimicrobial surfactant polymer of claim 1 wherein the polymer backbone comprises polyvinyl amine.

4. The antimicrobial surfactant of claim 1 wherein the hydrophilic side chain comprises an average molecular weight of less than 8,000 daltons.

5. A method of making the antimicrobial surfactant polymer of claim 1, the method comprising:
   a) providing a polymeric backbone of repeating monomeric units;
   b) providing a plurality of hydrophobic side chains comprising from about 2 to about 18 methylene groups;
   c) providing an antimicrobial peptide comprising Nisin;
   d) providing a first hydrophilic side chain and a second hydrophilic side chain having a proximal chain end spaced from a distal chain end comprising reactionable di-aldehyde terminated polyethylene glycols;
   e) attaching the plurality of hydrophobic side chains to the polymeric backbone by one of the group consisting of ester linkages, secondary amine linkages, amide linkages, and combinations thereof;
   f) attaching the proximal chain end of the first and second hydrophilic side chains to the polymeric backbone by one of the group consisting of ester linkages, secondary amine linkages, amide linkages, and combinations thereof; and
   g) attaching the distal chain end of at least one of the first or second hydrophilic side chains to the antimicrobial peptide by an aldehyde linkage.

6. The method of claim 5, wherein the antimicrobial peptide is selected from the group consisting of Nisin A, Nisin Z, Nisin Q, Nisin F, Nisin U, and combinations thereof.

7. The method of claim 5 including providing the polymer backbone comprising polyvinyl amine.

8. A method of applying an antimicrobial surfactant polymer to a substrate surface, the method comprising:
   a) providing an antimicrobial surfactant polymer, comprising:
      i) a polymeric backbone of repeating monomeric units;
      ii) a plurality of hydrophobic side chains comprising from about 2 to about 18 methylene groups, the plurality of hydrophobic side chains being linked to the polymeric backbone by one of the group consisting of ester linkages, secondary amine linkages, amide linkages, and combinations thereof;
      iii) a first hydrophilic side chain and a second hydrophilic side chain comprising reactionable di-aldehyde terminated polyethylene glycol molecules, the first and second side chains each having a proximal hydrophilic side chain end linked to the polymeric backbone by one of the group consisting of ester linkages, secondary amine linkages, amide linkages, and combinations thereof spaced from a distal hydrophilic side chain end;
      iv) an antimicrobial peptide comprising Nisin having an aldehyde linkage linked to the distal chain end of at least one of the first or second hydrophilic side chains by the aldehyde linkage; and
   b) dissolving the antimicrobial surfactant polymer in deionized water to form an antimicrobial surfactant solution; and
   c) exposing a surface of a substrate to the antimicrobial surfactant solution.

9. The method of claim 8 including dissolving the antimicrobial surfactant polymer in deionized water to a concentration of about 0.2% by volume.

10. The method of claim 8 including exposing the surface of the substrate to the antimicrobial surfactant solution for about 10 to about 20 hours at a temperature ranging from about 35° C. to about 45° C.

11. The method of claim 8, wherein the substrate comprises an exterior surface of a medical device.

12. The method of claim 11, wherein the medical device is selected from the group consisting of a catheter, an introducer, medical lead, a cardiac defibrillator, a cardiac pacemaker, a neuro-stimulator, a drug pump, a blood pump, a heart valve, an orthopedic implant, and an orthopedic tool.

13. The method of claim 8, wherein the antimicrobial peptide is selected from the group consisting of Nisin A, Nisin Z, Nisin Q, Nisin F, Nisin U, and combinations thereof.

14. The method of claim 8, wherein the polymer backbone comprises polyvinyl amine.

* * * * *